United States Patent [19]

Bailey

[11] Patent Number: 5,254,475
[45] Date of Patent: Oct. 19, 1993

[54] SEQUENTIAL C-TERMINAL DEGRADATION OF PEPTIDES AND PROTEINS

[75] Inventor: Jerome M. Bailey, Duarte, Calif.

[73] Assignee: City of Hope, Duarte, Calif.

[21] Appl. No.: 856,151

[22] PCT Filed: Jun. 21, 1991

[86] PCT No.: PCT/US91/04434

§ 371 Date: May 31, 1992

§ 102(e) Date: May 31, 1992

Related U.S. Application Data

[63] Continuation-in-part of Ser. No. 576,943, Aug. 13, 1990, Pat. No. 5,059,540.

[51] Int. Cl.$^5$ .................................................. G01N 33/68
[52] U.S. Cl. .............................. 436/89; 530/345; 530/402; 530/408; 530/815

[58] Field of Search .............. 436/89; 530/345, 402, 530/408, 815, 816

[56] References Cited

U.S. PATENT DOCUMENTS

| 4,582,875 | 4/1986 | Ngo ........................... 525/54.11 |
| 4,837,165 | 6/1989 | Hawke ........................ 436/89 |
| 4,935,494 | 6/1990 | Miller ........................ 530/345 |
| 4,994,373 | 2/1991 | Stavrianopoulos et al. ...... 435/6 |
| 5,180,807 | 12/1991 | Bailey et al. ................ 530/345 |

Primary Examiner—James C. Housel
Assistant Examiner—David Redding
Attorney, Agent, or Firm—Edward S. Irons

[57] ABSTRACT

Reagents and method for the C-terminal sequencing of proteins and peptides are disclosed. The reagents include sodium trimethylsilanolate and trimethyl N-oxide. Derivatized, activated polyethylene supports for peptide samples subjected to C-terminal sequencing are described.

1 Claim, 10 Drawing Sheets

TRIMETHYLAMINE N-OXIDE

PEPTIDE THIOHYDANTOIN $(CH_3)_3SiO^- Na^+$

+

AQUEOUS TFA

THIOHYDANTOIN LEUCINE

SHORTENED PEPTIDE

Peptide Thiohydantoin

+

Thiohydantoin Amino Acid

+

Shortened Peptide

SEQUENTIAL C-TERMINAL DEGRADATION OF PEPTIDES AND PROTEINS

This application is a continuation-in-part of Bailey application Ser. No. 07/576,943 filed Aug. 13, 1990, now U.S. Pat. No. 5,059,540, which in turn is a continuation-in-part of PCT/US90/02723 filed May 18, 1990, each of which is incorporated herein by reference.

FIELD OF THE INVENTION

This invention relates to the sequential degradation of peptides and proteins from the carboxy-terminus. More particularly, the invention relates to a method for the cleavage of the C-terminal thiohydantoin amino acid from the derivatized peptide which results from the use of a silylisothiocyanate as a coupling reagent in carboxy-terminal sequencing procedures. The invention also relates to derivatized and activated supports for covalent immobilization of peptides to be sequenced.

BACKGROUND OF THE INVENTION

A. Background

The development of methods for the sequential degradation of proteins and peptides from the carboxy-terminus has been the objective of several studies. See Ward, C. W., *Practical Protein Chemistry - A Handbook* (Darbre, A., ed.) (1986) and Rangarajan, M., *Protein/Peptide Sequence Analysis: Current* (1988). Such a method would complement existing N-terminal degradations based on the Edman chemistry. Edman, P., *Acta. Chem. Scand.* 4:283-293 (1950). The most widely studied method and probably the most attractive because of its similarity to the Edman degradation has been the conversion of amino acids into thiohydantoins. This reaction, originally observed by Johnson and Nicolet, *J. Am. Chem. Soc.* 33:1973-1978 (1911), was first applied to the sequential degradation of proteins from the carboxy-terminus by Schlack and Kumpf, *Z. Physiol. Chem.* 154:125-170 (1926). These authors reacted ammonium thiocyanate, dissolved in acetic acid and acetic anhydride, with N-benzoylated peptides to form carboxyl-terminal 1-acyl-2-thiohydantoins. Exposure to strong base was used to liberate the amino acid thiohydantoin and generate a new carboxyl-terminal amino acid. The main disadvantages of this procedure have been the severity of the conditions required for complete derivatization of the C-terminal amino acid and for the subsequent cleavage of the peptidylthiohydantoin derivative into a new shortened peptide and an amino acid thiohydantoin derivative.

Since this work was published, numerous groups have tried to reduce the severity of the conditions required, particularly in the cleavage of the peptidylthiohydantoin, in order to apply this chemistry to the sequential degradation of proteins from the carboxyl terminal end. Lesser concentrations of sodium hydroxide than originally used by Schlack and Kumpf and of barium hydroxide were found to effectively cleave peptidylthiohydantoins. See Waley, S. G., et al., *J. Chem. Soc.* 1951:2394-2397 (1951); Kjaer, A., et al., *Acta Chem. Scand.* 6:448-450 (1952); Turner, R. A., et al., *Biochim. Biophys. Acta.* 13:553-559 (1954). Other groups used acidic conditions based on the original procedure used by Johnson and Nicolet for the de-acetylation of amino acid thiohydantoins. See Tibbs, J., *Nature* 168:910 (1951); Baptist, V. H., et al., *J. Am. Chem. Soc.* 75:1727-1729 (1953). These authors added concentrated hydrochloric acid to the coupling solution to cause cleavage of the peptidylthiohydantoin bond. Unlike hydroxide which was shown to cause breakdown of the thiohydantoin amino acids, hydrochloric acid was shown not to destroy the amino acid thiohydantoins. See Scoffone, E., et al., *Ric. Sci.* 26:865-871 (1956); Fox, S. W., et al., *J. Am. Chem. Soc.* 77:3119-3122 (1955); Stark, G. R., *Biochem.* 7:1796-1807 (1968). Cromwell, L. D., et al., *Biochem.* 8:4735-4740 (1969) showed that the concentrated hydrochloric acid could be used to cleave the thiohydantoin amino acid at room temperature. The major drawback with this procedure was that when applied to proteins, no more than two or three cycles could be performed.

Yamashita, S., *Biochem. Biophys. Acta.* 229:301-309 (1971) found that cleavage of peptidylthiohydantoins could be done in a repetitive manner with a protonated cation exchange resin. Application of this procedure to 100 mmol quantities of papain and ribonuclease was reported to give 14 and 10 cycles, respectively, although no details were given. See Yamashita, S., et al., *Proc. Hoshi. Pharm.* 13:136-138 (1971). Stark reported that certain organic bases, such as morpholine or piperidine, could be substituted for sodium hydroxide, and along the same lines, Kubo, H., et al., *Chem. Pharm. Bull.* 19:210-211 (1971) reported that aqueous triethylamine (0.5M) could be used to effectively cleave peptidylthiohydantoins. Stark appeared to have solved the cleavage problem by introducing acetohydroxamic acid in aqueous pyridine at pH 8.2 as a cleavage reagent. This reagent was shown to rapidly and specifically cleave peptidylthiohydantoins at room temperature and at mild pH.

Conditions for the formulation of the peptidylthiohydantoins were improved by Stark and Dwulet, F. E., et al., *Int. J. Peptide and Protein Res.* 13:122-129 (1979), who reported on the use of thiocyanic acid rather than thiocyanate salts, and more recently by the introduction of trimethylsilylisothiocyanate (TMS-ITC) as a coupling reagent. See Hawke, D. H., et al., *Anal. Biochem.* 166:298-307 (1987). The use of this reagent for C-terminal sequencing has been patented. See Hawke U.S. Pat. No. 4,837,165. This reagent significantly improved the yields of peptidylthiohydantoin formation and reduced the number of complicating side products. Cleavage of peptidylthiohydantoins by 12N HCl (Hawke, 1987) and by acetohydroxamate (Miller, C. G., et al., *Techniques in Protein Chemistry* (Hugli, T. E., ed.) pp. 67-68, Academic Press (1989)) failed to yield more than a few cycles of degradation.

B. The Cleavage Problem

Although the cleavage reaction has been extensively studied since the thiocyanate chemistry for C-terminal degradation was first proposed by Schlack and Kumpf in 1926, a chemical method has not yet been proposed that is capable of an extended degradation. Cleavage in 1N sodium hydroxide as first proposed by Schlack and Kumpf (1926) is well known to hydrolyze proteins and peptides at other sites in addition to cleavage of the C-terminal peptidylthiohydantoin. The released thiohydantoin amino acid derivatives are also known to be unstable in hydroxide solutions. Scoffone, supra. Cleavage by hydroxide is known to convert the side chain amide groups of asparagine and glutamine residues to a carboxylic group making these residues indistinguishable from aspartate and glutamate, respectively.

When cleavage of peptidylthiohydantoins by 12N HCl was applied to proteins and peptides no more than 2 or 3 cycles could be performed. See, Cromwell, supra and Hawke, supra. This was probably due to differences in the rate of hydrolysis of peptidylthiohydantoins containing different amino acid side chains as well as to hydrolysis of other internal amide bonds. Likewise, during the synthesis of the standard amino acid thiohydantoin derivatives corresponding to the naturally occurring amino acids, it was observed that the rate of deacetylation of the N-acetylthiohydantoin amino acids by 12 HCl depended on the nature of the amino acid side chain. Bailey, J. M., et al. Biochem. 29:3145-3156 (1990).

Attempts by Dwulet, supra, to reproduce the resin based cleavage method of Yamashita, supra, was reported to be unsuccessful. Cleavage of peptidylthiohydantoins with aqueous methanesulfonic acid was also attempted by Dwulet and by Bailey, et al., both without success. Methanesulfonic acid was chosen since it is equivalent to the acidic group on the resin employed by Yamashita (1971) and Yamashita, et al. (1971).

Cleavage of the peptidylthiohydantoin derivatives with acetohydroxamate as originally reported by Stark, supra, was found to result in the formation of stable hydroxamate esters at the C-terminus of the shortened peptide (Bailey, et al., supra). Depending on the conditions employed, between 684 and 93% of the peptide was derivatized at the C-terminus and thus prevented from further sequencing. Although Stark, supra, predicted such hydroxamate esters to form as an intermediate during cleavage, it was assumed that they would break down under the conditions used for cleavage or continued sequencing. The peptidyl hydroxamate esters formed from cleavage with acetohydroxamate, like the hydroxamate esters studied by Stieglitz, J., et al., *J. Am. Chem. Soc.* 36:272-301 (1914) and Scott, A. W., et al., *J. Am. Chem. Soc.* 49:2545-2549 (1927), are stable under the acidic conditions used for thiohydantoin formation and can only be hydrolyzed to a free peptidyl carboxylic group, capable of continued sequencing, under strongly basic conditions. This probably explains the low repetitive yields of Stark, supra; Meuth, J. L., et al., *Biochem.* 21:3750-3757 (1982) and Miller, supra, when aqueous acetohydroxamate was employed as a cleavage reagent.

Cleavage of peptidylthiohydantoins by aqueous triethylamine was originally reported by Kubo, H., et al., *Chem. Pharm. Bull.* 19:210-211 (1971), Dwulet, et al., supra, and Meuth, et al., supra. The latter group commented on the usefulness of triethylamine as a cleavage reagent for automated sequencing because of its volatility, but declined to pursue this method apparently in favor of cleavage by acetohydroxamate. Cleavage of peptidylthiohydantoins, in the solution phase, by a 2% aqueous solution of triethylamine was found to be rapid (half-times of 1 min. and 5 min. at 37° C. and 22° C., respectively) and quantitative, yielding only shortened peptide capable of continued sequencing and the amino acid thiohydantoin derivative. Bailey, et al., supra.

The automation of C-terminal sequencing requires prolonged (1 to 10 days) storage of reagents in glass bottles at room temperature within the instrument. The reagents used for sequencing must be stable to these conditions. Storage of triethylamine in water rapidly results in the breakdown of the triethylazine. These breakdown products include primary and secondary amines which can subsequently block the shortened peptide from further sequencing. Free radical compounds are also formed during the breakdown of triethylamine. These free radical compounds are often UV absorbing and can interfere with the subsequent HPLC detection of the released thiodydantoin amino acid. Applicant's experience with using aqueous triethylamine (5% triethylamine in water) for automated C-terminal sequencing has consistently resulted in repetitive yields no higher than 60%, thereby permitting no more than three cycles of C-terminal degradation to be performed on peptides covalently coupled to PVDF or polyethylene membrane supports.

C. Peptide Sample Supports

In the preferred practice of the C-terminal sequencing chemistry of this invention, the peptide sample is covalently attached to a solid support. Applicant and others (Inglis et al., *Met. Protein Sequence Analysis* (Jornavall/Hoog/Gustavsson, Eds.) pp. 23-24, Birkhauser-Verlag, Basel (1991); Wittman-Liebold, et al., *Met. Protein Sequence Analysis* (Jornavall/Hoog/Gustavsson, Eds.) pp. 9-21, Birkhauser-Verlag, Basel (1991); Hawke and Boyd, *Met. Protein Sequence Analysis* (Jornavall/Hoog/Gustavsson, Eds.) pp. 35-45, Birkhauser-Verlag, Basel (1991)), have recognized that C-terminal chemistry is preferably applied to samples covalently attached, at the N-terminal, to a solid phase. Covalent immobilization of the sample on a solid support allows the use of reagents and solvents optimal for sequencing without causing sample washout, the capability to efficiently wash the sample to remove reaction by-products which might otherwise interfere with identification of the released thiohydantoin amino acids, and prevents mechanical losses associated with most solution phase methods. In general, automated solid phase chemistry is expected to be more efficient and less labor intensive compared to manual solution phase methods.

Since the introduction of the solid-phase approach to N-terminal protein sequencing by Laursen, R. A. *J. Amer. Chem. Soc.*, 88:5344-5346 (1966), several different types of functionalized supports have been described for the covalent immobilization of polypeptide samples. These include polystyrene resins, polyacrylamide resins, and glass beads substituted with aminoalkyl or aminophenyl groups (Laursen and Machleidt, *Methods Biochem. Anal.* 26:201-284 (1980); Machleidt, *Modern Methods in Protein Chemistry* (Tschesche, H., Ed.) pp. 262-302, de Gruyter, Berlin/New York (1983)). Typically these amino functionalized supports are activated for protein coupling with bifunctional reagents such as phenylene disothiocyanate (DITC). The DITC group is capable of forming a stable thiourea linkage to the support and the peptide N-terminal amino group or epsilon amino group of side chain lysines. Recently glass beads derivatized with isothiocyanato, ainophenyl and aminethylaminopropyl groups (Song-Ping Liang and Laursen, *Anal. Biochem.* 188:366-373 (1990)), glass fibre sheets functionalized with aminphenyl groups (Aebersold et al., *Anal. Biochem.* 187:56-65 (1990)), and PVDF (polyvinylidene difluoride) membranes derivatized with aryl amines and DITC (Pappin et al., *Current Research in Protein Chemistry* (Villafranca, J. J., Ed.) pp. 191-202, Academic Press, Inc. (1990)) have been used for the covalent immobilization of polypeptides for N-terminal sequencing. The polypeptides are either immobilized by coupling between the epsilon amino groups of the lysine and the isothiocyanate groups on the solid support using the established DITC chemistry or by the coupling of the activated C-terminal carboxyl groups of the polypeptides and the amino groups on the matrix.

Many of the initial studies involving the application of the thiocyanate chemistry for C-terminal sequencing to the solid phase have involved the use of glass beads for the covalent immobilization of peptide samples (Williams and Kassall, *FEBS Lett.* 54:353-357 (1975); Rangarajan and Darbre, *Biochem. J.* 157:307-316 (1976); Meuth et al., *Biochem.* 21:3750-3757 (1982); Hawke et al., *Anal. Biochem.* 166:298-307 (1987); Inglis, et al. *Methods in Protein Sequence Analysis* (Wittmann-Liebold, B., Ed.) pp. 137-144, Springer-Verlag (1989). More recent work has involved the use of carboxylic acid modified PVDF (Bailey and Shavely, *Techniques in Protein Chemistry: II* (Villafranca, J. J., Ed.) pp. 115-129, Academic Press, Inc. (1991)), DITC-activated amino PVDF (Miller et al., *Techniques in Protein Chemistry* (Hugli, T. E., Ed.) pp. 67-78, Academic Press, Inc. (1989), Inglis et al., *Met. Protein Sequence Analysis* (Jornval/Hoog/Gustavsson, Eds.) pp. 23-24, Birkhauser-Verlag, Basel (1991)), and a disuccinimidoyl carbonate polyamide resin (Hawke and Boyd, *Met. Protein Sequence Analysis* (Jornvall/Hoog/Gustavsson, Eds.) pp. 35-45, Birkhauser-Verlag, Basel (1991).

The use of glass and PVDF supports for C-terminal sequencing is attended by disadvantages. Siloxane bonds are formed on derivatization of the glass supports. These bonds are base labile resulting in loss of the covalently coupled peptide sample. The carboxyl modified PVDF and the DITC-activated amino PVDF are both physically and chemically altered adversely due to dehydro-fluorination (Dias and McCarthy, *Macromolecules* 17:2529-2531 (1984)) caused by the basic cleavage reagents used during the course of C-terminal sequencing. These membranes may turn successively darker and more brittle on each C-terminal sequencing cycle.

SUMMARY OF THE INVENTION

This invention provides novel C-terminal peptide cleavage reagents, including (i) alkali metal salts of lower trialkylsilanols and (ii) trialkylamine N-oxides. These novel cleavage reagents have particular utility in, but are not limited to, sequencing procedures in which a silyl isothiocyanate is used as the coupling reagent. Sodium trimethyl silanolate and trimethyl amine N-oxide are preferred. In the preferred practice of the invention the N-terminal of the peptide sample is covalently bound to an activated PE-COOH solid phase.

DETAILED DESCRIPTION OF THE INVENTION

The mechanism of acid and base hydrolysis of acylthiohydantoins was studied in detail by Congdon and Edward, *Can. J. Chem.* 50:3767-3788 (1972) and a number of cleavage reagents were tested by Stark, supra. Stark found that oxygen containing nucleophiles were the best choice of reagents to effect this reaction. Although acetohydroxamate is an excellent cleavage reagent for the first amino acid, it forms a stable peptidyl hydroxamate ester, which is difficult to remove, and which effectively blocks the shortened peptide from further sequencing. This reagent also results in a high UV absorbing background during subsequent HPLC identification of the released thiohydantoin amino acids. It seems that in general any carbon based reagent that is a good nucleophile and thus a good cleavage reagent will also be a poor leaving group, thereby blocking much of the shortened peptide from further sequencing.

Figure 1:
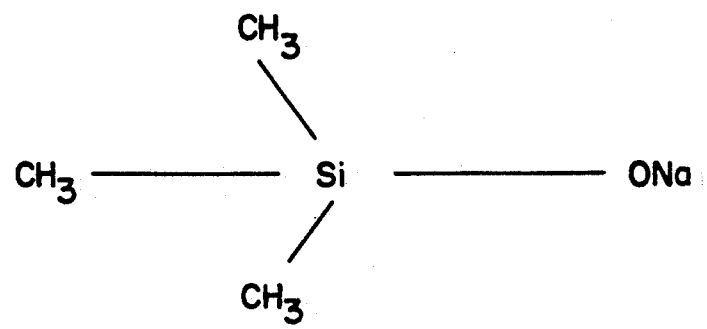
FIG. 1 is the formula of sodium trimethylsilanolate.
Figure 2:
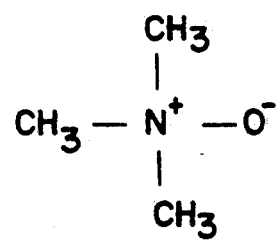
FIG. 2 is the formula of trimethylamine N-oxide.

Ideally, a cleavage reagent should possess the following characteristics: (1) it should be able to cleave peptidylthiohydantoins in a volatile, water miscible organic solvent, thus eliminating the problems of incompatibility of PVDF membranes with water; (2) the reaction should be rapid and specific; (3) the shortened peptide should be capable of continued degradation; (4) the released thiohydantoin amino acid should not be destroyed by this reagent; and (5) this reagent should not absorb light in the same range as is used for detection of the released thiohydantoin amino acid derivatives. Sodium trimethylsilanolate (FIG. 1), commercially available from Petrarch (Huls), in, e.g., alcoholic solvents, and trimethyl amine N-oxide (FIG. 2) commercially available from Aldrich Chemical co. in alcoholic and a wider range of solvents seem to possess all of these characteristics. Cleavage of peptidylthiohydantoins in the solution phase with a 0.05M solution of sodium trimethylsilanolate in 100% methanol or trimethylsilylethanol is complete in less than 5 minutes. A 0.05M solution of sodium trimethylsilanolate in methanol or trimethylsilylethanol effects cleavage of peptidylthiohydantoins both in the solution phase and in the solid phase in less than 5 minutes.

More specifically, this invention contemplates the use of the cleavage reagents of this invention in a concentration of from about 0.025 molar to about 0.25 molar, preferably from about 0.1 to about 0.2 molar, in methanol, trimethylsilylethanol or similar alcohols or, in the case of trimethylamine N-oxide, a wider range of solvents.

Figure 3:
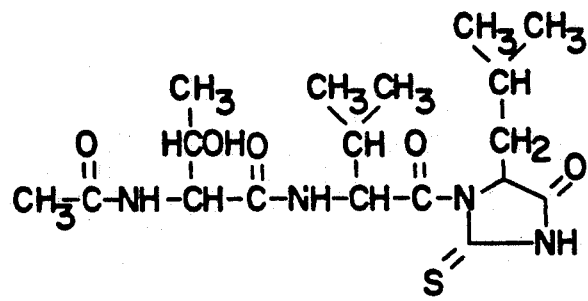
FIG. 3 is the postulated mechanism of the cleavage reaction with sodium trimethylsilanolate and the use of aqueous acid, e.g., trifluoroacetic acid (TFA), following the cleavage reaction.
Figure 3:
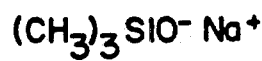
Figure 3:
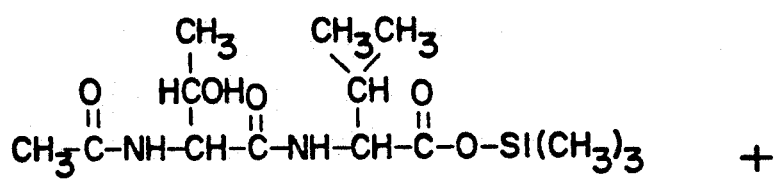
Figure 3:
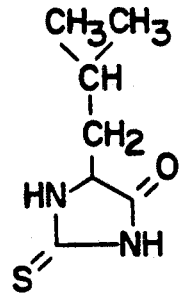
Figure 3:
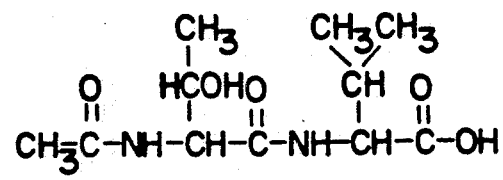
Figure 3A:
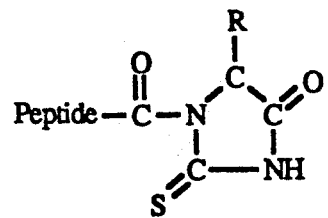
FIG. 3A shows an analogous mechanism in which sodium trimethyl silanolate is used following the cleavage reaction.
Figure 3A:
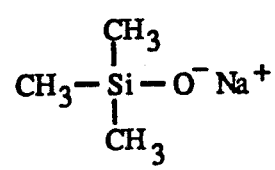
Figure 3A:
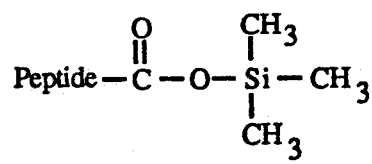
Figure 3A:
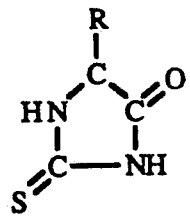
Figure 3A:
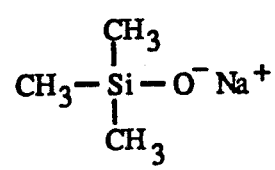
Figure 3A:
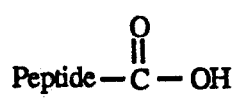
Figure 3A:
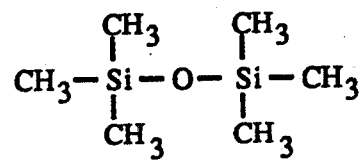

The most probable mechanism of this cleavage involves formation of an unstable C-terminal trimethylsilyl ester which, in the presence of water or alcohol, rapidly reforms the desired C-terminal carboxylic group. See FIG. 3 which illustrates the use of aqueous trifluoroacetic acid (TFA) following the cleavage reaction. Preferably, the concentration of TFA in this step is from about 0.01M to about 0.2M. The use of TFA or an equivalent acid at this stage significantly facilitates cleavage.

In its more broad aspects, the invention includes cleavage reagents having the formula $R_3SiO^-X^+$, in which R is a straight or branched chain hydrocarbon radical having from about 1 to about 10 carbon atoms and X is an alkali metal ion, preferably a sodium or a potassium ion.

The broader aspects of the invention also include trimethylamine N-oxides in which the alkyl groups have from one to about four carbon atoms. Triethyl, tripropyl, triisopropyl, tributyl or triisobutyl amine N-oxides may be used. Such reagents have the formula $(R_1)_3 N^+-O^-$, in which $R_1$ is an alkyl group having from one to about four carbon atoms.

Suitable supports include activated carboxylic acid modified non-porous preferably polyethylene films or membrane. This support for C-terminal sequencing, hereinafter generally identified as PE-COOH, offers a number of advantages over the existing supports. These include: (1) stability of the support to the conditions employed for C-terminal sequencing; (2) the ability, due to the hydrophilic nature of the surface groups, to use both aqueous and organic solvents for performing chemistry on covalently coupled polypeptide samples; (3) a high capacity (3.2 nmoles/mm$^2$ of surface area) to covalently couple polypeptides; (4) the convenient size (1×5 mm) of the support needed for sequencing is similar to that employed in applicant's continuous flow reactor for automated N-terminal sequencing.

The PE-COOH films useful as supports in the present invention are typically 1 mil thick with a range of from 0.5 to 20 mils thick. The films are non-porous and naturally hydrophobic. A preferred method for preparing PE-COOH from polyethylene films is described in detail in U.S. Pat. No. 4,339,473, which is incorporated herein by reference. These PE-COOH films are commercially available from Pall Corporation, 30 Sea Cliff Avenue, Glen Cove, N.Y. 11542 under the tradename PERMION.

PE-COOH such as the "PERMION" product of Pall Corporation is activated by the formation of an ester derivative with which the N-terminus of the peptide sample may be coupled. Appropriate activation reagents include 1,3-dicyclohexylcarbodiimide (DCC), 1,1'-carbonyldiimidazole (CDI), 1-ethyl-3-(3-dimethylamiopropyl) carbodiimide hydrochloride (EDC), benzotriazol-1-yl-oxy-tris(dimethylamino)phosphonium hexafluorophosphate (BOP), 1,3-Diisopropylcarbodiimide (DICD).

In general, activation of PE-COOH is accomplished by reaction for an appropriate time, e.g. about two hours, with a solution of an activating agent in a suitable solvent at about room temperature.

Table I is illustrative.

TABLE I

Effect of Different Coupling Reagents And Solvents on the Yield of Leucine Enkephalin Coupled to PE-COOH

| Activating Reagent | nmol covalently coupled to membrane (% yield) | |
|---|---|---|
| | 50% acetonitrile | 50% DMF |
| DCC | 0.2 (4.4) | 1.8 (39.6) |
| CDI | 0.07 (1.5) | 0.23 (5.1) |
| EDC | 0.32 (6.9) | 0.12 (2.6) |
| BOP | 0.58 (12.7) | 0.29 (6.4) |

TABLE I-continued

Effect of Different Coupling Reagents And Solvents on the Yield of Leucine Enkephalin Coupled to PE-COOH

| Activating Reagent | nmol covalently coupled to membrane (% yield) | |
|---|---|---|
| | 50% acetonitrile | 50% DMF |
| DICD | 0.68 (15.0) | 0.57 (12.6) |

DCC - 1,3-dicyclohexylcarbodiimide
CDI - 1,1' carbonyldiimidazole
EDC - 1-ethyl-3-(3-dimethylamiopropyl) carbodiimide hydrochloride
BOP - benzotriazol-1-yl-oxy-tris(dimethylamino) phosphonium hexafluorophosphate
DICD - 1,3-Diisopropylcarbodiimide A strip of PE-COOH (1 cm×0.1 cm) was placed in a 1.5 cm continuous flow reactor (CFR) (Shavely, et al., 1987) sealed at one end. The membranes were reacted with 30 µl (30 mmol) of the activating reagent for 30 min. at room temperature. The solvent used in all cases was 100% DMF, except for when EDC was the activating agent, when water was the solvent. After the activation reaction, excess reagent was washed away with the solvent used for the activation reaction (3 ml). Each sample was then washed with acetonitrile (1 ml) and dried in a vacuum centrifuge. The activated membranes were then reacted with a 30 µl solution (4.54 nmol) of the peptide, YGGFL, in either 50% aqueous DMF or 50% aqueous acetonitrile in a CFR reactor (sealed at one end) for 16 hours. The membranes were washed with either 50% acetonitrile or 50% DMF, followed by acetonitrile, and then dried in a vacuum centrifuge. The amount of coupled peptide was determined by amino acid compositional analysis of the derivatized membrane.

Table II reports the effect of activation time and coupling time on the yield of covalent attachment of YGGFL.

TABLE II

Effect of Activation Time and Coupling Time on the Yield of Covalent Attachment of YGGFL

| Activation Time (hrs) | Coupling Time (hrs) | Amount Coupled (nmol) | Yield |
|---|---|---|---|
| 0.5 | 1 | 0.54 | 4.0 |
| 0.5 | 2 | 2.11 | 15.6 |
| 0.5 | 4 | 3.33 | 24.7 |
| 0.5 | 20 | 5.19 | 38.4 |
| 1.0 | 1 | 1.01 | 7.5 |
| 1.0 | 2 | 1.59 | 11.8 |
| 1.0 | 4 | 2.73 | 20.2 |
| 1.0 | 20 | 5.57 | 41.3 |
| 2.0 | 1 | 2.44 | 18.1 |
| 2.0 | 2 | 2.45 | 18.1 |
| 2.0 | 4 | 5.25 | 38.9 |
| 2.0 | 20 | 7.2 | 53.3 |
| 4.0 | 1 | 0.52 | 3.9 |
| 4.0 | 2 | 0.52 | 3.9 |
| 4.0 | 4 | 3.4 | 25.2 |
| 4.0 | 20 | 4.1 | 30.4 |

The membranes (1×12.5 mm) were activated by an excess of DCC in anhydrous DMF (1 g/1 ml) for 2 hours. At the end of the activation reaction, the excess reagent was removed with anhydrous DMF and the activated membrane strip dried in a vacuum centrifuge. Each activated membrane was inserted into a continuous flow reactor (CFR) (Shavely et al., Anaylytical Biochemistry (1987) 163, 517–529) containing a 100 µl solution of leucine enkephalin (13.5 nmol) in 50% aqueous DMF for the indicated time at 22° C. The microbore tubing on one end of the CFR was sealed by first heating and then pinching closed with pliers. After the coupling reaction, the membrane was rinsed with coupling solvent and acetonitrile, and then dried in a vacuum centrifuge. The amount of covalently coupled peptide was determined by amino acid analysis.

An important aspect of the invention, preferred for the C-terminal sequencing of peptides consisting of a large number of amino acid residues entail the addition of a linker arm, of the general formula $NH_2(CH_2)_n COCH$, wherein n is between 4 and 10 to the PE-COOH carboxyls followed by covalent attachment of the peptide sample to the linker arm carboxyl. Where linker arms are utilized the PE-COOH carboxyls are preferably activated with 2-fluoro-1-methylpyridine to facilitate attachment to the linker molecule. See generally Mukaiyama, *Angewandte Chemie* 18:707–721 (1979). The linker carboxyls are activated in the manner described for PE-COOH carboxyls.

EXPERIMENTAL PROCEDURES

Materials. Acetic anhydride was purchased from Fisher Chemical Co. Trimethylsilylisothiocyanate (TMS-ITC), anhydrous dimethylformamide (DMF), Benzotriazol-1-yl-oxy-tris(dimethylamino)phosphoniumhexaflurophosphate (BOP), 1,3-Diisopropylcarbodiimide (DIIC), and 1,1'-Carbonyldiimidazole (CDI) were from Aldrich. Water was purified on a Millipore Milli Q system. All of the peptides used in this study were either obtained from Bachem or Sigma. 1,3-Dicylcohexylcarbodiimide (DCC), 1-ethyl-3-(3-dimethylaminopropyl)-carbodiimide (EDC), and triethylamine (sequanal grade) were obtained from Pierce. The carboxylic acid modified polyethylene membranes (PE-COOH) were provided by the Pall Corporation (Long Island, N.Y.). The amino acid thiohydantoins used in this study were synthesized as described (Bailey and Shavely, *Biochemistry* 29:3145–3156 (1990).

Covalent Coupling of Peptides to Carboxylic Acid Modified PVDF. A piece of PVDF-COOH (1 cm×0.1 cm) was placed in a continuous flow reactor (CFR) (Shavely, et al. *Anal. Biochem.* 163:517–529 (1987)), 2 μl of 1,3-dicyclohexylcarbodiimide (DCC) (2 mmol/ml) in N,N-dimethylformamide (DMF) was added through a Hamilton syringe. The microbore tubing on one end of the CFR was sealed by first heating and then pinching closed with pliers. The CFR was then placed in a sealed eppendorf tube. After a two hour activation (25° C.), the activated membrane was rinsed with 2 ml of DMF and then dried under a stream of argon. Leucine enkephalin (2 μl of a 14 nmol/μl solution in DMF) was carefully layered on the dry membrane and allowed to react overnight. The membrane was washed with methanol (5 ml) and dried under a stream of argon. The yield of coupled peptide was determined, after acid hydrolysis of the derivatized membrane, by amino acid composition analysis. Typical yields were approximately 50%.

Covalent Coupling of Peptides to Carboxylic Acid Modified Polyethylene. A piece of PE-COOH (1×12.5 mm) was placed in a continuous flow reactor (CFR) (Shavely, et al., (1987) supra), and activated an excess of 1,3-dicylohexylcarbodiimide in anhydrous DMF (1 g/ml) for 2 hours. The microbore tubing on one end of the CFR was sealed by first heating and then pinching closed with pliers. The CFR was then placed in a sealed eppendorf tube. At the end of the activation reaction, the excess reagent was washed off with anhydrous DMF and dried in a vacuum centrifuge. Each activated membrane was again inserted into a continuous flow reactor (CFR) (Shavely, et al., (1987) supra) containing the peptide solution of interest and incubated overnight (20 hours) at 22° C. The capacity of the CFR used was 100 μl. After the coupling reaction, the membrane was rinsed with coupling solvent and acetonitrile, and then dried in a vacuum centrifuge.

Use of this new reagent for cleavage in a 1:1 solution of methanol and tert-butanol as a solvent has allowed the automated sequencing of several peptides covalently coupled to a support such as a polyethylene or PVDF membrane. Examples are shown for the peptides, KVILF, YGGFMRGL, YGGFL, and RGYALG. In this case the thiohydantoin of arginine co-elutes with the only major background peak. The combination of methanol with tert-butanol is the preferred solvent for the cleavage reaction. Other alcoholic solvents useful in the invention include alkanols having from one to six atoms, e.g. ethanol, isopropanol, 2-trimethylsilylethanol and isobutanol.

EXEMPLIFICATION OF THE C-TERMINAL SEQUENCING INVENTION

Figure 9:
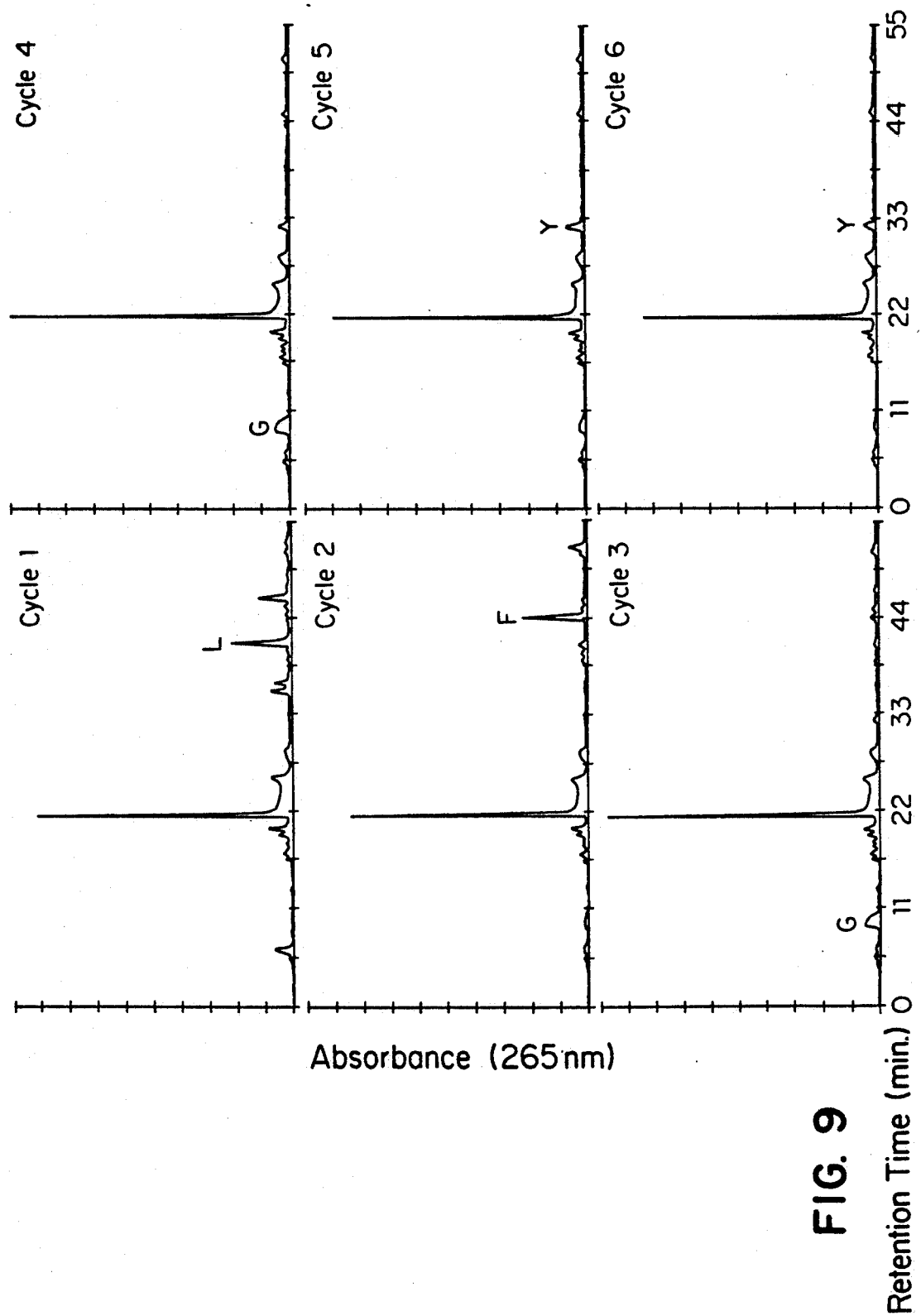
FIG. 9 shows the sequencing from the C-terminal of the peptide (YGGFL) covalently coupled to a linker 11-amino undecaonic acid.

The examples described herein illustrate C-terminal sequencing accomplished with a modified N-terminal sequencer based on the design of Hawke, et al., *Anal. Biochem.* 147:315–330 (1985), in which a continuous flow reactor as described in Shavely U.S. patent application Ser. No. 072,754 was utilized. FIG. 9 is the schematic of the instrument used to perform all of the examples. Release of thiohydantoin amino acids was detected by an on-line HPLC. See Shively, *Anal. Biochem.* 163:517–529 (1987). The reagent and solvent delivery system were all constructed from perfluoro-elastomers. Delivery valves as generally described in U.S. Pat. No. 4,530,586 provided with electromagnetically actuated solenoids and zero dead volume were connected in a modular fashion providing multiple input to a single output line. The valves which control the flow of reagents and solvents are computer operated pursuant to a program appropriate for the chemistry involved.

Table III is a program summary for the C-terminal sequencer illustrated by FIG. 9 and used to perform the experiment described in the Example.

TABLE III

| C-Terminal Sequencer Program Summary | | |
|---|---|---|
| Continuous Flow Reactor (CFR)(65° C.) | Conversion Flask (CF)(55° C.) | Duration (sec) |
| S1 reaction | | 120 |
| S1 reaction | | 120 |
| | R4 rinse | 120 |
| Dry | Dry | 100 |
| R1 reaction | | 180 |
| R2 reaction | | 450 |
| S4 rinse | | 60 |
| R1 reaction | | 180 |
| R2 reaction | | 450 |
| S4 rinse | | 60 |
| R1 reaction | | 180 |
| R2 reaction | | 450 |
| S4 rinse | | 60 |
| R1 reaction | | 180 |
| R2 reaction | | 450 |
| S4 rinse | | 120 |
| S2 rinse | | 60 |
| S4 rinse | | 120 |
| S3 rinse | | 120 |
| S4 rinse | | 120 |
| R3 reaction | | 1200 |
| R3 to CF | | 45 |
| R3 reaction | Dry | 240 |
| R3 reaction | Dry | 240 |
| S2 delivery | | 12 |

TABLE III-continued

C-Terminal Sequencer Program Summary

| Continuous Flow Reactor (CFR)(65° C.) | Conversion Flask (CF)(55° C.) | Duration (sec) |
| --- | --- | --- |
| S2 reaction |  | 120 |
| S2 to CF |  | 45 |
| S2 delivery |  | 11 |
| S2 reaction |  | 120 |
| S2 to CF |  | 45 |
|  | inject | 7 |
| pause | pause | 60 |

EXAMPLE 1

Sequencing of Leucine Enkephalien (YGGFL) (1.2 nmoL) Covalently Coupled to PVDF-COOH The composition of the reagents and solvents is set forth in Table IV.

TABLE IV

Composition of Reagents and Solvents

| | |
| --- | --- |
| R1 | Acetic anhydride |
| R2 | 30% TMS-ITC in acetonitrile |
| R3 | 0.05M Sodium trimethylsilanolate in 2-trimethylsilylethanol |
| R4 | Methanol |
| S1 | Acetonitrile |
| S2 | 0.8% Trifluoroacetic acid in water |
| S3 | Methanol |
| S4 | — |

Activated PVDF-COOH understood to be described in U.S. Pat. No. 5,611,861, was obtained from Pall Corporation. The thiohydantoin amino acid derivatives were separated by reverse phase HPLC. This separation was performed on Phenomenex Ultracarb 5 ODS(30) column (2.0 mm×25 mm) on a Beckman System Gold with a Shimadzu (SPD-6A) detector. The column was eluted for 2 min with solvent A (0.1% trifluoroacetic acid in water) and then followed by a discontinuous gradient to solvent B (80% acetonitrile, 10% methanol in water) at a flow rate of 0.15 mL/min at 22° C. The gradient used was as follows: 0% B for 2 min, 0–6% B over 3 min, 6–35% B over 35 min, 35–50% B over 10 min, and 50–0% B over 10 min.

Figure 4:
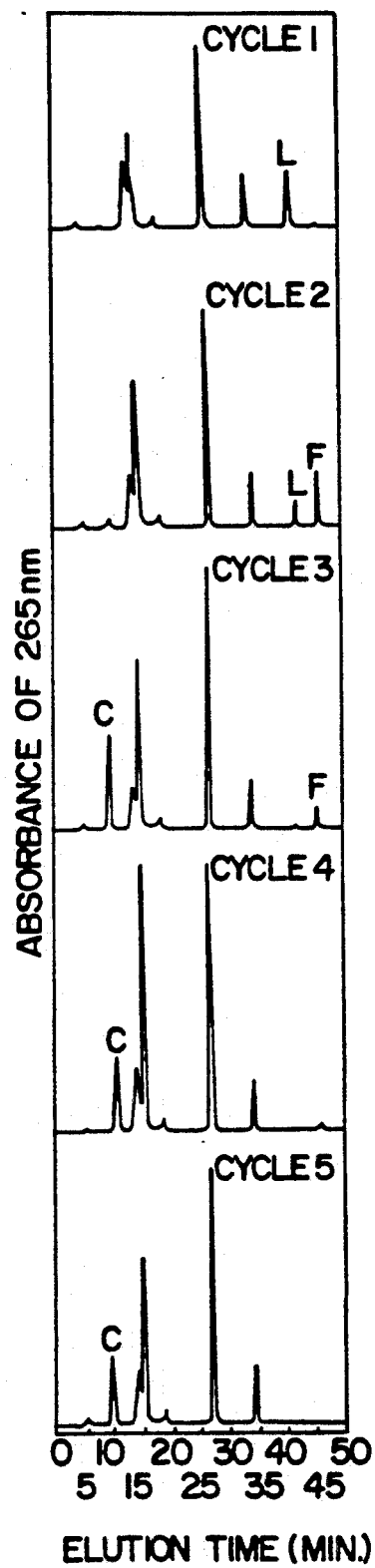
FIG. 4 shows the sequencing of leucine-enkephalin (YGGFL) covalently coupled to PVDF.

FIG. 4 depicts the HPLC analysis of products of the reaction.

EXAMPLE 2

Sequencing of KVILF (1.2 nmol) Covalently Coupled to PVDF-COOH

The composition of the reagents and solvents is set forth in Table V.

TABLE V

Composition of Reagents and Solvents

| | |
| --- | --- |
| R1 | Acetic anhydride |
| R2 | 30% TMS-ITC in acetonitrile |
| R3 | 0.05M Sodium trimethylsilanolate in methanol |
| R4 | Methanol |
| S1 | Acetonitrile |
| S2 | 0.8% Trifluoroacetic acid in water |
| S3 | — |
| S4 | — |

The thiohydantoin amino acid derivatives were separated by reverse phase HPLC. This separation was performed on Phenomenex Ultracarb 5 ODS(30) column (2.0 mm×25 mm) on a Beckman System Gold with a Shimadzu (SPD-6A) detector. The column was eluted for 2 min with solvent A (0.1% trifluoroacetic acid in water) and then followed by a discontinuous gradient to solvent B (80% acetonitrile, 10% methanol in water) at a flow rate of 0.15 mL/min at 22° C. The gradient used was as follows: 0% B for 2 min, 0–6% B over 3 min, 6–354 B over 35 min, 35–50% B over 10 min, and 50–0% B over 10 min.

Figure 5:
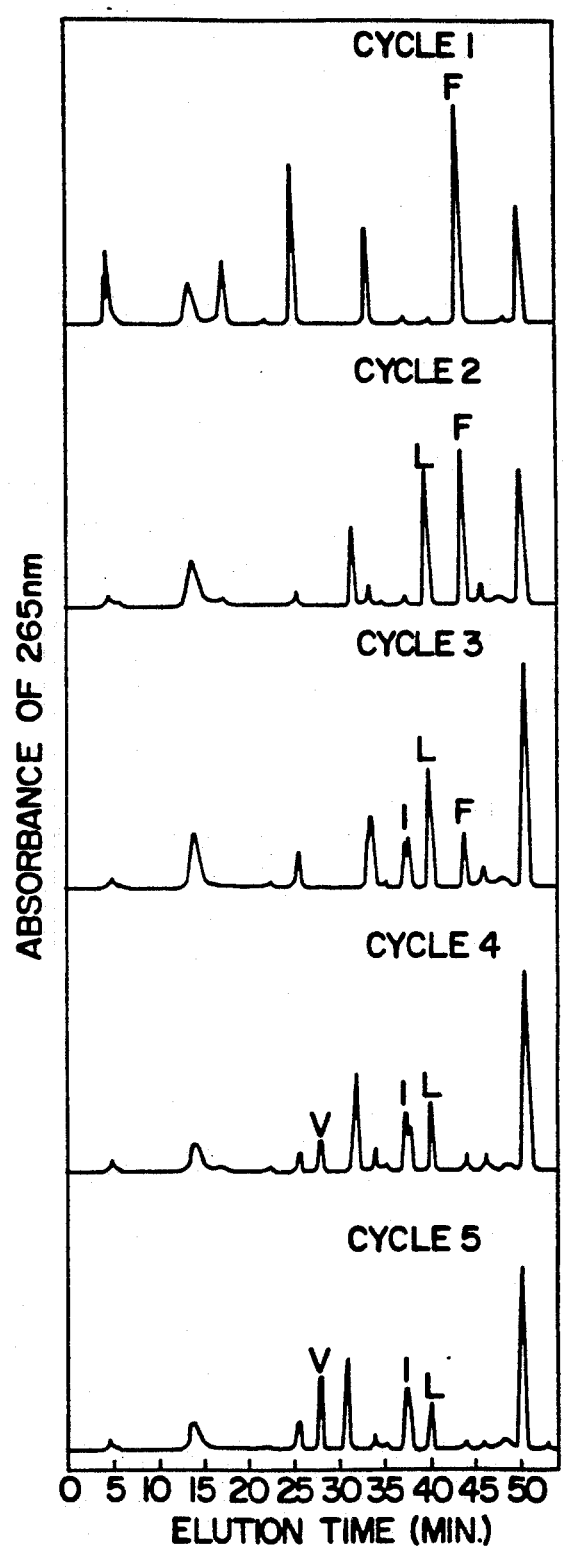
FIG. 5 shows the sequencing from the C-terminal of KVILF covalently attached to a PVDF membrane.

FIG. 5 depicts the HPLC analysis of products of the reaction.

EXAMPLE 3

Sequencing of Leucine Enkephalin (YGGFL) (24.2 nmol) Covalently Coupled to Polyethylene The composition of the reagents and solvents is set forth in Table VI.

TABLE VI

Composition of Reagents and Solvents

| | |
| --- | --- |
| R1 | Acetic anhydride |
| R2 | 30% TMS-ITC in acetonitrile (v/v) |
| R3 | 0.10M Sodium trimethylsilanolate in 50% methanol, 50% t-butyl alcohol |
| R4 | Methanol |
| S1 | 5% Triethylamine in water |
| S2 | 1.0% Trifluoroacetic acid in water |
| S3 | 50% Methanol, 50% Water |
| S4 | Acetonitrile |

The thiohydantoin amino acid derivatives were separated by reverse phase HPLC. The separation was performed on a Phenomenex Ultracarb 5 ODS(30) column (2.0 mm×25 mm) on a Beckman 126 Pump Module with a Shimadzu (SPD-6A) detector. The column was eluted for 5 min with solvent A (0.006% phosphoric acid, 0.006% triethylamine, 0.045% pentanesulfonic acid) and then followed by a discontinuous gradient to solvent B (0.03% phosphoric acid, 0.0454 triethylamine, 30% acetonitrile, 0.045% pentanesulfonic acid) at a flow rate of 0.15 mL/min at 22° C. The gradient used was as follows: 0% B for 5 min, 0–20% B over 7 min, 20–1004 B over 25 min, 100% for 23 min, and 100–0% B over 2 min.

Figure 6:
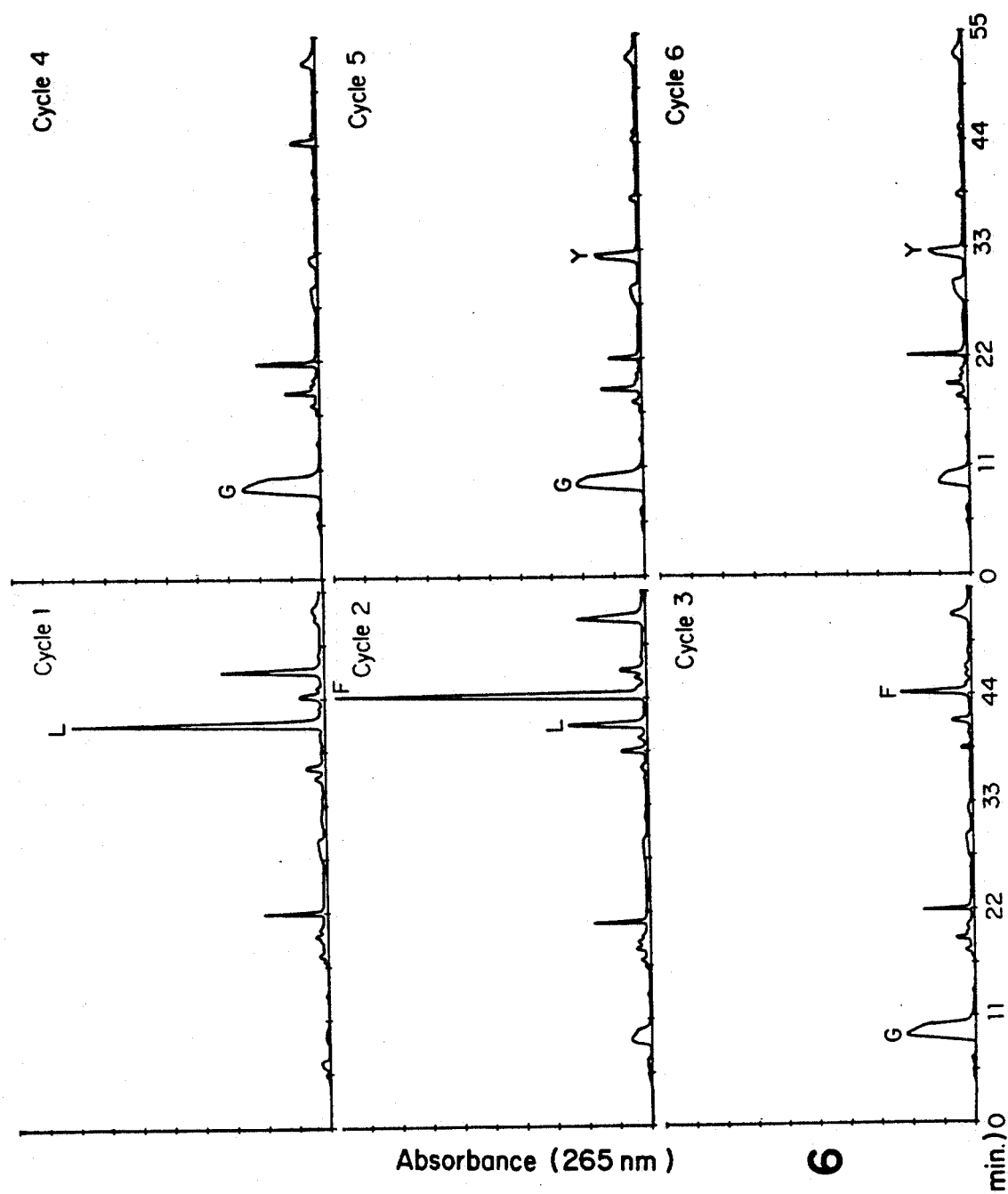
FIG. 6 shows the sequencing from the C-terminal of the peptide (YGGFL) covalently coupled to an activated PE-COOH membrane.

FIG. 6 depicts the results of the HPLC analyses.

EXAMPLE 4

Sequencing of RGYALG (8.1 nmol) Covalently Coupled to PE-COOH

The sequencing of RGYALG was performed exactly as described in Example 3.

Figure 7:
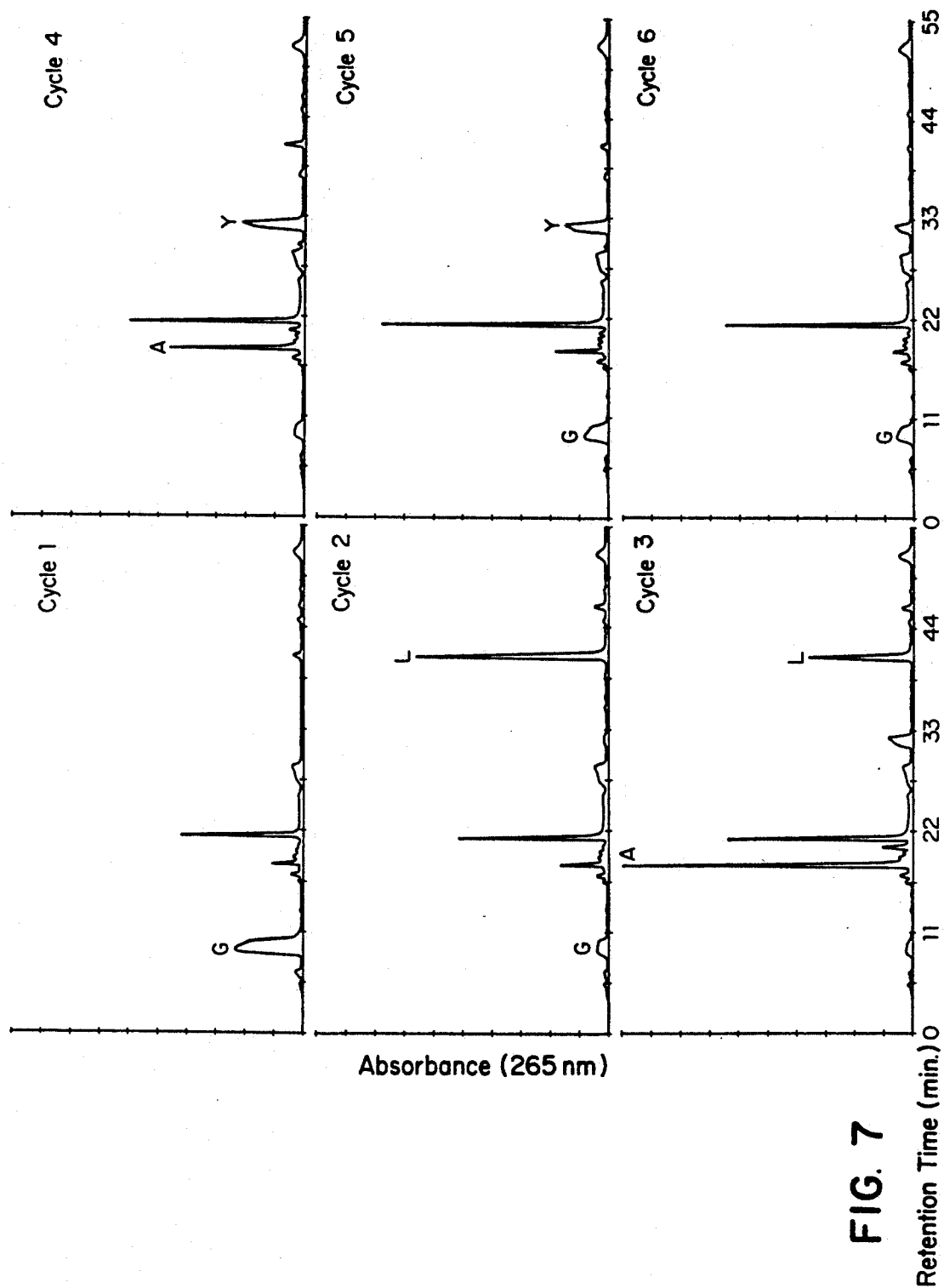
FIG. 7 shows the sequencing from the C-terminal of the peptide (RGYALG) covalently coupled to an activated PE-COOH membrane.

FIG. 7 depicts the HPLC analyses.

EXAMPLE 5

Sequencing of YGGFMRGL (9.6 nmol) Covalently Coupled to PE-COOH

The sequencing of YGGFMRGL was performed exactly as described in Example 4.

Figure 8:
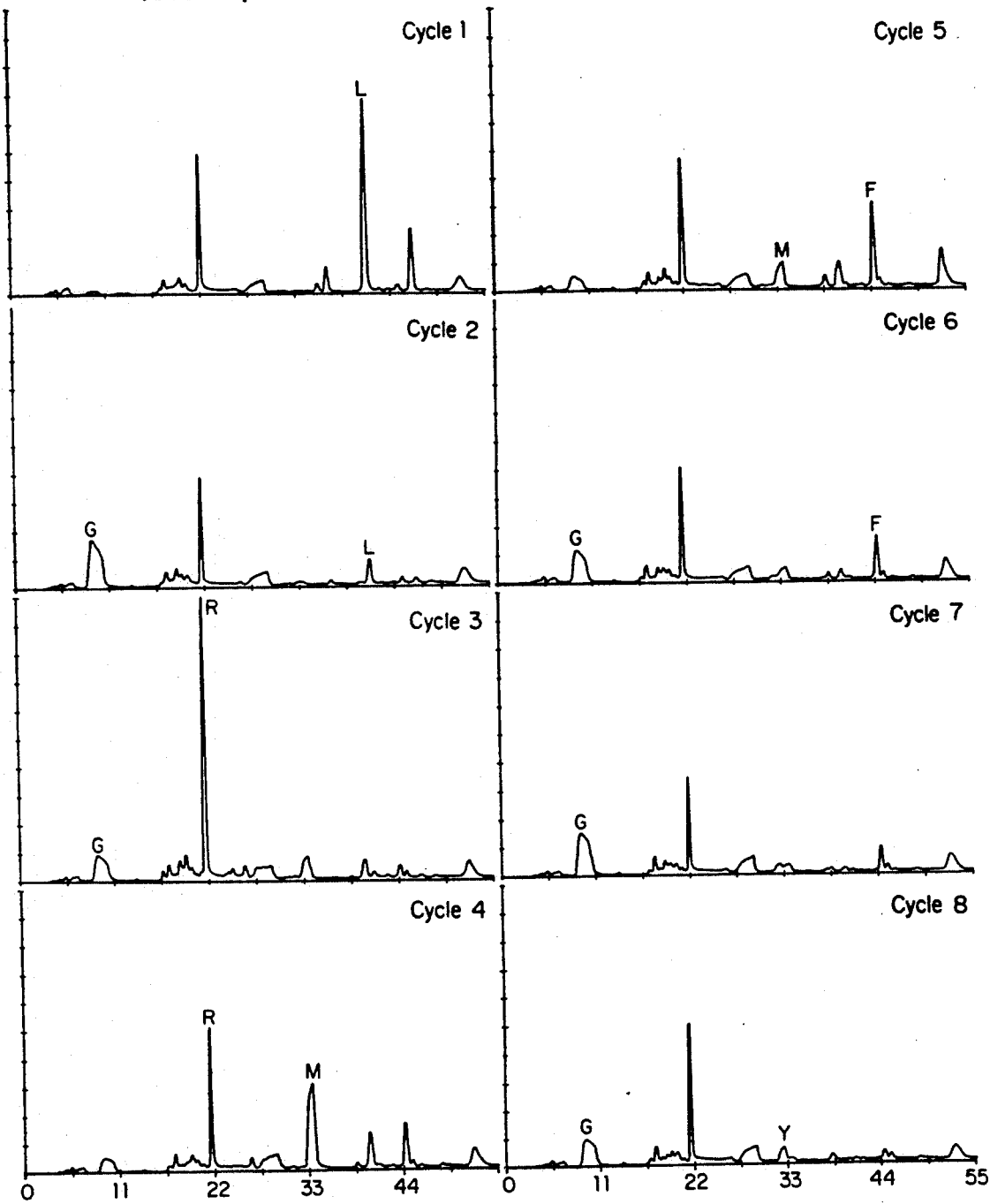
FIG. 8 shows the sequencing from the C-terminal of the peptide (YGGFMRGL) covalently coupled to an activated PE-COOH membrane.

FIG. 8 depicts the HPLC analyses.

EXAMPLE 6

Sequencing of YGGFL (3.7 mol)

Covalently Coupled to the Linker 11-Aminoundecanoic Acid $H_2N(CH_2)_{10}CO_2H$

Figure 10:
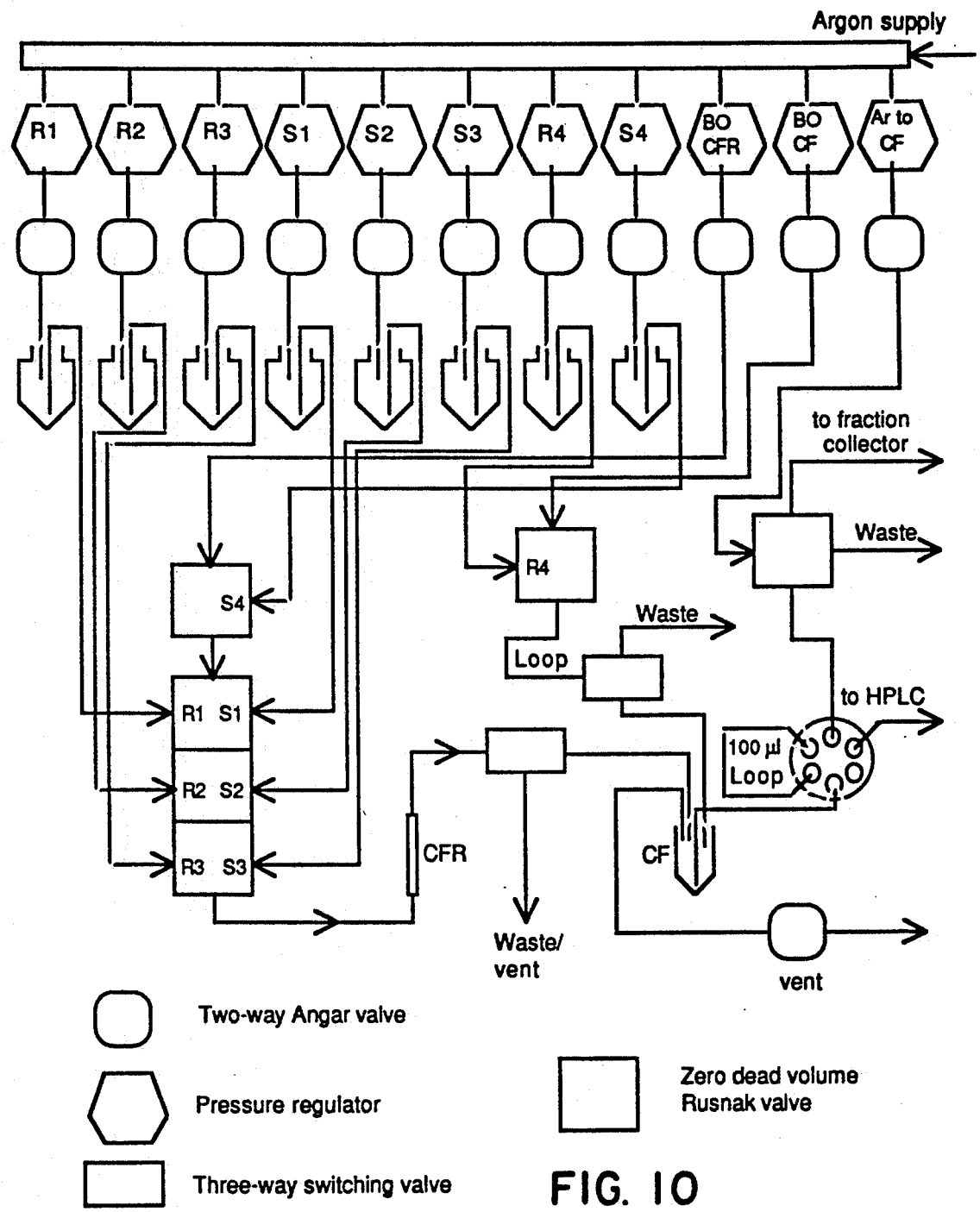
FIG. 10 is a schematic of the instrument used for C-terminal sequencing.

FIG. 9 depicts the sequencing from the C-terminal of the peptide YGGFL (3.7 mol) covalently coupled to the linker 11-aminoundecaonic acid $H_2N(CH_2)_{10}CO_2H$. The linker was attached to PE-COOH by activation of the PE-COOH carboxyl groups with DCC as described. After attachment, the linker carboxyl groups were similarly activated with DCC and the peptide then covalently attached. In the absence of linkers after six cycles of sequencing, 50% of the N-terminal amino acid, Y, is still covalently attached when sequencing the peptide YGGFL (FIG. 6). When the same peptide is sequenced after attachment to the above mentioned linker (FIG. 10), using the same sequencing protocol, only 12% of the N-terminal amino acid, Y is still covalently attached.

The sequencing of YGGFL was performed exactly as described in Example 3.

What is claimed is:

1. A method for sequencing a peptide by carboxyl terminal degradation which comprises coupling the carboxyl terminus of a peptide with a coupling reagent to form a peptidylthiohydantoin derivative and cleaving the peptidylthiohydantoin derivative with a reagent having the formula $R_3SiO^-X^+$, in which R is a straight or branched chain hydrocarbon radical having from about 1 to about 10 carbon atoms and X is an alkali metal ion to provide a thiohydantoin derivative of the amino acid previously at the carboxyl terminus of a peptide and a peptidyl residue lacking such an amino acid, the N-terminal of said peptide being covalently coupled to an activated, carboxylic acid modified, polyethylene membrane.

* * * * *